(12) United States Patent
Lavedan et al.

(10) Patent No.: US 9,074,256 B2
(45) Date of Patent: Jul. 7, 2015

(54) METHOD OF PREDICTING A PREDISPOSITION TO QT PROLONGATION

(75) Inventors: Christian Lavedan, Potomac, MD (US); Simona Volpi, Derwood, MD (US); Louis Licamele, Potomac, MD (US)

(73) Assignee: Vanda Pharmaceuticals, Inc., Washington, DC (US)

( * ) Notice: Subject to any disclaimer, the term of this patent is extended or adjusted under 35 U.S.C. 154(b) by 311 days.

(21) Appl. No.: 13/263,076

(22) PCT Filed: Apr. 5, 2010

(86) PCT No.: PCT/US2010/029943
§ 371 (c)(1),
(2), (4) Date: Nov. 28, 2011

(87) PCT Pub. No.: WO2010/117941
PCT Pub. Date: Oct. 14, 2010

(65) Prior Publication Data
US 2012/0035215 A1 Feb. 9, 2012

Related U.S. Application Data

(60) Provisional application No. 61/167,139, filed on Apr. 6, 2009.

(51) Int. Cl.
*C12Q 1/68* (2006.01)
*A61K 31/519* (2006.01)

(52) U.S. Cl.
CPC .......... *C12Q 1/6883* (2013.01); *A61K 31/519* (2013.01); *C12Q 2600/156* (2013.01)

(58) Field of Classification Search
None
See application file for complete search history.

(56) References Cited

U.S. PATENT DOCUMENTS

| 5,364,866 A | 11/1994 | Strupczewski et al. |
| 5,658,911 A | 8/1997 | Strupczewski et al. |
| 6,140,345 A | 10/2000 | Strupczewski et al. |
| 2006/0073506 A1 | 4/2006 | Christians et al. |
| 2011/0077539 A1 | 3/2011 | George et al. |

FOREIGN PATENT DOCUMENTS

| WO | 9309276 A1 | 5/1993 | |
| WO | 9511680 A1 | 5/1995 | |
| WO | 0124681 A2 | 4/2001 | |
| WO | 03016504 A2 | 2/2003 | |
| WO | 03020707 A1 | 3/2003 | |
| WO | 03016504 A2 | 7/2003 | |
| WO | 03062791 A2 | 7/2003 | |
| WO | 2004057030 A2 | 7/2004 | |
| WO | 2006039663 A2 | 4/2006 | |
| WO | WO2006/009663 * | 4/2006 | ............ 435/6 |
| WO | 2006039663 A3 | 11/2006 | |
| WO | 2006124646 A2 | 11/2006 | |
| WO | 2006131528 A2 | 12/2006 | |
| WO | 2006131528 A3 | 3/2007 | |
| WO | 2006124646 A3 | 8/2007 | |

OTHER PUBLICATIONS

Juppner; Bone, vol. 17; 1995, pp. 39S-40S.*
Lucentini (The Scientist; 2004, vol. 24, p. 20).*
Hegele (Arterioscler. Thromb. Vasc. Biol.; 2002, vol. 22, pp. 1058-1061).*
Volpi et al; 57th Annual meeting of the American Society of Human Genetics, 2007, Abstract.*
Levine et al; Formulary Journal, Jun. 1, 2008, pp. 1-7.*
ss66391863, for rs7067971 (dbSNP, NCBI, NLM; 2006).*
Albers et al; Expert Opin. Investig. Drugs. 2008, vol. 17, pp. 61-75.*
Cussac, International Application No. PCT / US2010 / 029931, PCT International Preliminary Report on Patentability, dated Apr. 6, 2009, 7 pages.
Nickitas-Etienne, International Application No. PCT / US2010 / 029945, PCT International Preliminary Report on Patentability, dated Apr. 6, 2009, 7 pages.
Nickitas-Etienne, International Application No. PCT / US2010 / 029943, PCT International Preliminary Report on Patentability, dated Apr. 6, 2009, 7 pages.
Lindner, International Application No. PCT / US2010 / 029921, PCT International Preliminary Report on Patentability, dated Apr. 6, 2009, 7 pages.
Chiang et al., "The Long QT Syndromes: Genetic Basis and Clinical Implications," Jul. 2000, pp. 1-12, Journal of American College of Cardiology, vol. 36, No. 1 (XP002590440).
Donger et al., "KVLQT1 C-Terminal Missense Mutation Causes a Forme Fruste Long-QT Syndrome," Nov. 1997, pp. 2778-2781, American Heart Association, vol. 96, No. 9 (XP002922668).
Liu et al., "KCNQ1 and KCNH2 Mutations Associated with Long QT Syndrome in a Chinese Population," Nov. 2002, pp. 1-7, Human Mutation, Mutation in Brief, vol. 20, No. 6 (XP002590441).
Volpi et al., "Whole Genome Association Study Identifies Polymorphisms Associated with QT Prolongation During Iloperidone Treatment of Schizophrenia," Jun. 2008, pp. 1024-1031, Molecular Psychiatry, vol. 14, No. 11 (XP002590482).
Yang et al., "Allelic Variants in Long-QT Disease Genes in Patients With Drug-Associated Torsades de Pointes," Apr. 2002, pp. 1943-1948, Circulation downloaded from: circ.ahajournals.org at the European Patent Office.
Patent Cooperation Treaty, PCT Notification of Transmittal of the International Search Report and the Written Opinion of the International Searching Authority, or the Declaration for PCT/US2010/029921 dated Aug. 19, 2010, 15 pages.
Cohen et al., "Cloning and Characterization of FAM13A1—A Gene Near a Milk Protein QTL on BTA6: Evidence for Population-Wide Linkage Disequilibrium in Israeli Holsteins," Aug. 2004, pp. 374-383, Genomics 84, Academic Press, available online at: www.sciencedirect.com.
Patent Cooperation Treaty, PCT Notification of Transmittal of the International Search Report and the Written Opinion of the International Searching Authority, or the Declaration for PCT/US2010/029931 dated May 27, 2010, 13 pages.

(Continued)

*Primary Examiner* — Jehanne Sitton
(74) *Attorney, Agent, or Firm* — Hoffman Warnick LLC

(57) ABSTRACT

The present invention describes an association between genetic polymorphisms in the ABCC2 gene and a predisposition to prolongation of the QT interval, and provides related methods for the prediction of such a predisposition, the administration of QT interval-prolonging compounds to individuals having such a predisposition, and determining whether a compound is capable of inducing QT prolongation.

10 Claims, No Drawings

(56) References Cited

OTHER PUBLICATIONS

Cascorbi, "Role of Pharmacogenetics of ATP-Binding Cassette Transporters in the Pharmacokinetis of Drugs," Nov. 2006, pp. 457-473, Pharmacology & Therapeutics, Science Direct, vol. 112, No. 2.
Patent Cooperation Treaty, PCT Notification of Transmittal of the International Search Report and the Written Opinion of the International Searching Authority, or the Declaration for PCT/US2010/029943 dated Jul. 5, 2010, 14 pages.
Fujita et al., "Association of ATP-Binding Cassette, Sub-Family C, No. 2 (ABCC2) Genotype with Pharmacokinetics of Irinotecan in Japanese Patients with Metastatic Colorectal Cancer Treated with Irinotecan Plus Infusional 5-Fluorouracil/Leucovorin (FOLFIRI)," Nov. 2008, pp. 2137-2142, Biological & Pharmaceutical Bulletin, vol. 31, No. 11 (XP007913544).
Derosse et al., "The Genetics of Symptom-Based Phenotypes: Toward a Molecular Classification of Schizophrenia," Jul. 2008, pp. 1047-1043, Schizophrenia Bulletin, vol. 34, No. 6 (XP007913527).
Patent Cooperation Treaty, PCT Notification of Transmittal of the International Search Report and the Written Opinion of the International Searching Authority, or the Declaration for PCT/US2010/029945 dated Jul. 7, 2010, 13 pages.
ss66324480, rs3775378, dbSNP Short Genetic Variations, NCBI, NLM, 2006, 5 pages.
ss66046634, rs1083338, dbSNP Short Genetic Variations, NCBI, NLM, 2007, 5 pages.
Sitton, Office Action Communication for U.S. Appl. No. 13/263,075 dated Oct. 8, 2013, 23 pages.
Sitton, Office Action Communication for U.S. Appl. No. 13/263,077 dated Nov. 7, 2013, 25 pages.
Mueller, Frank, Patent Application No. 10713287.0 Office Action dated Jun. 11, 2014, 6 pages.
Sitton, Office Action Communication for U.S. Appl. No. 131/263,074 date Jan. 13, 2014, 28 pages.
GenBank, *Homo sapiens* KVLQt1 Gene, GenBank:AJ006345.1, NCBI, 88 pages, 2006.
Sitton, Office Action Communication for U.S. Appl. No. 13/263,075 dated Mar. 20, 2014, 11 pages.
Sitton, Office Action Communication for U.S. Appl. No. 13/263,077 dated Mar. 27, 2014, 11 pages.

* cited by examiner

METHOD OF PREDICTING A PREDISPOSITION TO QT PROLONGATION

CROSS-REFERENCE TO RELATED APPLICATIONS

This application claims the benefit of co-pending U.S. Provisional Patent Application No. 61/167,139, filed 6 Apr. 2009, which is hereby incorporated herein.

BACKGROUND OF THE INVENTION

1. Technical Field

The invention relates generally to a method of predicting an individual's predisposition to QT prolongation, and more particularly, to a method of predicting such predisposition based on a sequence of the individual's ABCC2 (ATP-binding cassette, sub-family C, member 2) gene.

2. Background

Prolongation of the electrocardiographic QT interval (the time between the start of the Q wave and the end of the T wave) is referred to as long QT syndrome (LQTS). LQTS may comprise a genetic component. In some patients with LQTS, QT prolongation can be a chronic condition. In some persons, LQTS may be induced by the administration of an active pharmaceutical ingredient that prolongs the QT interval. A number of compounds are believed to be capable of prolonging the QT interval. These include amiodarone, arsenic trioxide, bepridil, chloroquine, chlorpromazine, cisapride, clarithromycin, disopyramide, dofetilide, domperidone, droperidol, erythromycin, halofantrine, haloperidol, ibutilide, iloperidone, levomethadyl, mesoridazine, methadone, pentamidine, pimozide, procainamide, quinidine, sotalol, sparfloxacin, and thioridazine.

Other compounds are suspected of being capable of prolonging the QT interval, although such prolongation has not been definitively established. These include alfuzosin, amantadine, azithromycin, chloral hydrate, clozapine, dolasetron, felbamate, flecainide, foscarnet, fosphenytoin, gatifloxacin, gemifloxacin, granisetron, indapamide, isradipine, levofloxacin, lithium, moexipril, moxifloxacin, nicardipine, octreotide, ofloxacin, ondansetron, quetiapine, ranolazine, risperidone, roxithromycin, tacrolimus, tamoxifen, telithromycin, tizanidine, vardenafil, venlafaxine, voriconazole, and ziprasidone.

Individuals at risk of suffering LQTS are advised not to use still other compounds, due to the possibility that they may prolong the QT interval. These include albuterol, amitriptyline, amoxapine, amphetamine, dextroamphetamine, atomoxetine, chloroquine, ciprofloxacin, citalopram, clomipramine, cocaine, desipramine, dexmethylphenidate, dobutamine, dopamine, doxepin, ephedrine, epinephrine, fenfluramine, fluconazole, fluoxetine, galantamine, imipramine, isoproterenol, itraconazole, ketoconazole, levalbuterol, metaproterenol, methylphenidate, mexiletine, midodrine, norepinephrine, nortriptyline, paroxetine, phentermine, phenylephrine, phenylpropanolamine, protriptyline, pseudoephedrine, ritodrine, salmeterol, sertraline, sibutramine, solifenacin, terbutaline, tolterodine, trimethoprim-sulfa, and trimipramine.

By fluorescence in situ hybridization (FISH), Taniguchi et al. and van Kuijck et al. mapped the human MRP2/CMOAT gene to 10q24. Taniguchi et al., A human canalicular multispecific organic anion transporter (cMOAT) gene is overexpressed in cisplatin-resistant human cancer cell lines with decreased drug accumulation, *Cancer Res.* 56: 4124-4129, 1996. PubMed ID: 8797578; van Kuijck et al., Assignment of the canalicular multispecific organic anion transporter gene (CMOAT) to human chromosome 10q24 and mouse chromosome 19D2 by fluorescent in situ hybridization, *Cytogenet. Cell Genet.* 77: 285-287, 1997. PubMed ID: 9284939. Toh et al. determined the exon/intron structure of the human MRP2/CMOAT gene. They found that the human gene contains 32 exons and spans 200 kb or more genomic DNA. Toh et al., Genomic structure of the canalicular multispecific organic anion-transporter gene (MRP2/cMOAT) and mutations in the ATP-binding-cassette region in Dubin-Johnson syndrome, *Am. J. Hum. Genet.* 64: 739-746, 1999. PubMed ID: 10053008.

Evers et al., who referred to cMOAT as multidrug resistance-associated protein-2 (MRP2), studied its drug export activity in polarized kidney in MDCK cells. In contrast to MRP1, cMOAT was found predominantly intracellularly in nonpolarized cells, suggesting the cMOAT requires a polarized cell for plasma membrane routing. They found that when kidney epithelial MDCK cells were grown in a monolayer, cMOAT localized to the apical plasma membrane. Their studies demonstrated that cMOAT causes transport of organic anions, including a substrate not shown to be transported by organic anion transporters previously. Transport was inhibited only inefficiently by compounds known to block MRP1. They also showed that cMOAT caused transport of the anticancer drug vinblastine to the apical side of a cell monolayer. They concluded that cMOAT is a 5-prime-adenosine triphosphate binding cassette transporter that may be involved in drug resistance in mammalian cells. Evers et al., Drug export activity of the human canalicular multispecific organic anion transporter in polarized kidney MDCK cells expressing cMOAT (MRP2) cDNA, *J. Clin. Invest.* 101: 1310-1319, 1998. PubMed ID: 9525973.

SUMMARY OF THE INVENTION

The present invention describes an association between genetic polymorphisms in the ABCC2 gene and a predisposition to prolongation of the QT interval, and provides related methods for the diagnosis of such predisposition and for the administration of QT interval-prolonging compounds to individuals having such a predisposition.

A first aspect of the invention provides a method of administering to an individual a compound capable of prolonging the individual's QT interval, the method comprising determining at least a portion of an individual's ABCC2 gene sequence; and in the case that a portion of the individual's ABCC2 sequence is associated with an increased risk of QT prolongation, administering to the individual a quantity of the compound less than would be administered to an individual having a ABCC2 gene sequence not associated with an increased risk of QT prolongation, or electing instead to treat the individual with a different compound not known to be associated with QT prolongation.

A second aspect of the invention provides a method of determining whether or not an individual is predisposed to prolongation of the QT interval, the method comprising: determining at least a portion of an individual's ABCC2 gene sequence.

A third aspect of the invention provides a method of administering a compound capable of prolonging a QT interval to an individual suffering from long QT syndrome (LQTS), the method comprising: determining at least a portion of an individual's ABCC2 gene sequence; and administering to the individual a quantity of the compound based on the individual's ABCC2 gene sequence.

A fourth aspect of the invention provides a method of administering to an individual a compound capable of prolonging the individual's QT interval, the method comprising: characterizing an expression product of an individual's ABCC2 gene; and in the case that the characterized expression product is associated with an increased risk of QT prolongation, administering to the individual a quantity of the compound less than would be administered to an individual having an expression product not associated with an increased risk of QT prolongation. Expression products of the ABCC2 gene may include, for example, mRNA and protein including any isoform of the mRNA and protein.

A fifth aspect of the invention provides a method of determining whether an individual is predisposed to prolongation of the QT interval, the method comprising: characterizing an expression product of an individual's ABCC2 gene.

A sixth aspect of the invention provides a method of administering a compound capable of prolonging a QT interval to an individual suffering from long QT syndrome (LQTS), the method comprising: characterizing an expression product of an individual's ABCC2 gene; and administering to the individual a quantity of the compound based on the characterized expression product.

A seventh aspect of the invention provides a method of determining whether a compound is capable of prolonging QT interval in an individual, the method comprising: measuring an expression product of the individual's ABCC2 gene; administering to the individual a quantity of the compound; remeasuring the expression product of the individual's ABCC2 gene; and determining whether the compound is capable of prolonging the individual's QT interval based on a difference in the measurements of the expression product of the individual's ABCC2 gene.

An eighth aspect of the invention provides a method of determining whether a compound is capable of prolonging a QT interval in an individual, the method comprising: measuring a QT interval of each of a plurality of test organisms, the plurality including a first test organism having a ABCC2 genotype associated with a predisposition for prolongation of QT interval and a second organism having ABCC2 genotype not associated with a predisposition for prolongation of QT interval; administering a quantity of the compound to each of the plurality of test organisms; remeasuring a QT interval of at least the first test organism; and determining that the compound is capable of prolonging a QT interval in an individual in the case that the remeasured QT interval is greater than the measured QT interval. Test organisms may include, for example, humans, animal models, and/or cell lines.

DETAILED DESCRIPTION OF THE INVENTION

As indicated above, the invention provides a method of predicting an individual's predisposition to QT prolongation based on the sequence of the individual's ABCC2 (ATP-binding cassette, sub-family C, member 2) gene.

At least one single nucleotide polymorphisms (SNPs) within the ABCC2 gene has been found to have a significant correlation to a predisposition to drug-induced QT prolongation. Table 1, below, shows such SNPs and the genotypes associated with QT prolongation following the administration of iloperidone.

A genotype of GG at the rs7067971 locus was found to most accurately predict a predisposition to QT prolongation. This genotype is included amongst all genotypes associated with a predisposition to QT prolongation. Therefore, individuals having a genotype of GG at the rs7067971 locus may be considered predisposed to QT prolongation following the administration of a compound capable of prolonging the QT interval.

Since the QT interval changes with changes in heart rate, the QT interval is often measured as a corrected QT (QTc) interval. Any number of formulas may be employed to calculate the QTc, including, for example, the Fridericia formula (QTcF), the Bazett formula (QTcB), and the Rautaharju formula (QTp), among others. In the studies described herein, QT was calculated using the Fridericia formula. However, the present invention includes the use of any such formula or method for calculating a QTc or an uncorrected QT.

As noted above, a large number of compounds are known or suspected to be capable of inducing QT prolongation in some individuals, including individuals not suffering from LQTS. Such compounds may include compounds of Formula (1):

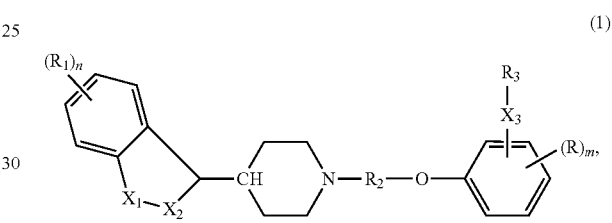

(1)

wherein:

R is, independently, hydrogen, lower alkyl, lower alkoxy, hydroxyl, carboxyl, lower hydroxyketone, lower alkanol, hydroxyl acetic acid, pyruvic acid, ethanediol, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoaklylaminocarbonyl, dialkylaminocarbonyl, formyl,

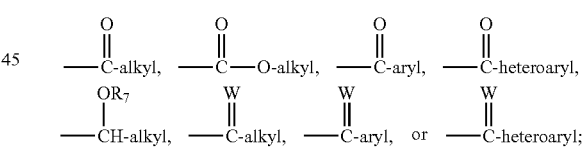

alkyl is lower alkyl, branched or straight and saturated or unsaturated;

TABLE 1

ABCC2 SNP Genotypes and QT Prolongation Following Administration of Iloperidone

| Affymetrix SNP No. | rs_number | Position | Lowest QTc change | P value | Allele A | Allele B |
|---|---|---|---|---|---|---|
| SNP_A-2253129 | rs4919395 | 101532953 | non-BB | 0.009208217 | C | T |
| SNP_A-2262953 | rs2804398 | 101548624 | non-BB | 0.000421121 | A | T |
| SNP_A-1928598 | rs2273697 | 101553805 | AB | 0.479636886 | C | T |
| SNP_A-1927451 | rs3740065 | 101595683 | AB | 0.760583618 | C | T |
| SNP_A-2068049 | rs7067971 | 101606569 | non-BB | 4.02462E-07 | A | G |
| SNP_A-4268713 | rs2256700 | 101623437 | non-BB | 0.595645464 | A | G |
| SNP_A-2004488 | rs2256678 | 101623769 | non-BB | 0.003956423 | C | T | acyl is lower alkyl or lower alkyloxy bonded through a carbonyl;

aryl is phenyl or phenyl substituted with at least one group, $R_5$, wherein each $R_5$ is, independently, hydrogen, lower alkyl, lower alkoxy, hydroxy, chlorine, fluorine, bromine, iodine, lower monoalkylamino, lower dialkylamino, nitro, cyano, trifluoromethyl, or trifluoromethoxy;

heteroaryl is is a five- or six-membered aryl ring having at least one heteroatom, $Q_3$, wherein each $Q_3$ is, independently, —O—, —S—, —N(H)—, or —C(H)=N—

W is $CH_2$ or $CHR_8$ or N—$R_9$;

$R_1$ is —H, lower alkyl, —OH, halo, lower alkoxy, trifluoromethyl, nitro, or amino;

$R_2$ is $C_2$-$C_5$ alkylene, alkenylene (cis or trans), or alkynylene, optionally substituted by at least one $C_1$-$C_6$ linear alkyl group, phenyl group or

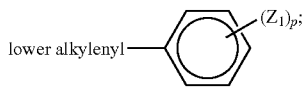

where $Z_1$ is lower alkyl, —OH, lower alkoxy, —$CF_3$, —$NO_2$, —$NH_2$, or halogen;

$R_3$ is lower alkyl or hydrogen;
$R_7$ is hydrogen, lower alkyl, or acyl;
$R_8$ is lower alkyl;
$R_9$ is hydroxy, lower alkoxy, or —$NHR_{10}$;
$R_{10}$ is hydrogen, lower alkyl, $C_1$-$C_3$ acyl, aryl,

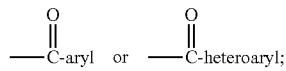

$X_1$, $X_2$, and $X_3$ are, independently, —O—, —S—, =N—, —N($R_3$)—, or $X_1$ and $X_2$ are not covalently bound to each other and are, independently, —OH, =O, —$R_3$, or =$NR_3$;

lower is 1-4 carbon atoms;
m is 1, 2, or 3; and
n is 1 or 2.

The compound may further include a compound of Formula (1) wherein:

R is —C(O)$CH_2$OH, —CH(OH)C(O)$CH_2$OH, —C(O)OH, CH(OH)$CH_3$, or C(O)$CH_3$;

$R_1$ is halo;

$X_1$ and $X_2$ are different and are =O, —OH, =N—, or —O—;

$R_2$ is $C_2$-$C_4$ alkylene or alkenylene;
$R_3$ is hydrogen, methyl, or ethyl;
$X_3$ is —O—; and
R is

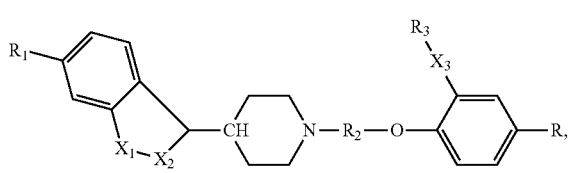

In a further embodiment, the compound may be iloperidone, which is also referred to as 1-[4-[3-[4-(6-fluoro-1,2-benzisoxazol-3-yl)-1-piperidinyl]propoxy]-3-methoxyphenyl]ethanone, as shown in Formula 1B:

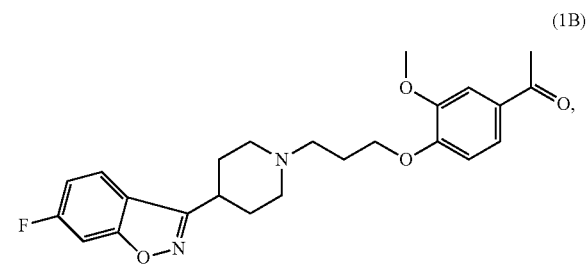 [SMILES: COc1cc(C(C)=O)ccc1OCCCN1CCC(c2noc3cc(F)ccc23)CC1]

Iloperidone is disclosed in U.S. Pat. Nos. 5,364,866, 5,658,911, and 6,140,345, each of which is incorporated herein by reference. Metabolites of iloperidone may also be capable of prolonging a QT interval. Metabolites of Iloperidone, e.g., 1-[4-[3-[4-(6-Fluoro-1,2-benzisoxazol-3-yl)-1-piperidinyl]propoxy]-3-methoxyphenyl]ethanol, as shown in Formula 1C:

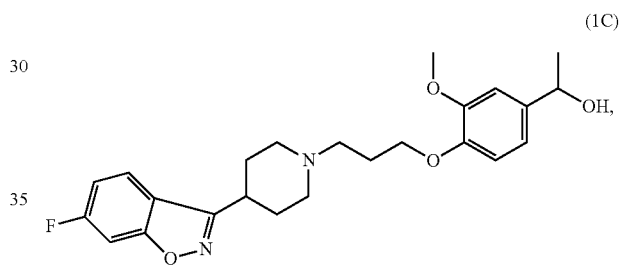

are described in International Patent Application Publication No. WO03020707, which is also incorporated herein by reference.

Other iloperidone metabolites include: 1-[4-[3-[4-(6-Fluoro-1,2-benzisoxazol-3-yl)-1-piperidinyl]propoxy]-3-hydroxyphenyl]ethanone; 1-[4-[3-[4-(6-Fluoro-1,2-benzisoxazol-3-yl)-1-piperidinyl]propoxy]-3-methoxyphenyl]-2-hydroxyethanone; 4-[3-[4-(6-Fluoro-1,2-benzisoxazol-3-yl)-1-piperidinyl]propoxy]-3-hydroxy-α-methylbenzene methanol; 4-[3-[4-(6-Fluoro-1,2-benzisoxazol-3-yl)-1-piperidinyl]propoxyl-2-hydroxy-5-methoxy-α-methylbenzenemethanol; 1-[4-[3-[4-(6-Fluoro-1,2-benzisoxazol-3-yl)-1-piperidinyl]propoxy]-2-hydroxy-5-methoxyphenyl]ethanone; and 1-[4-[3-[4-(6-Fluoro-1,2-benzisoxazol-3-yl)-1-piperidinyl]propoxy]-2,5-dihydroxyphenyl]ethanone. See U.S. Pat. No. 5,364,866 and International Patent Application Publication Nos. WO9309276 and WO9511680, which are incorporated herein by reference.

Using the genotypes at the SNP loci above, it is possible, with a high degree of certainty, to predict an individual's predisposition to QT prolongation. Table 2 below shows the results of a study of 174 individuals, each of whom was genotyped at the rs7067971 locus and their QT interval measured following the oral administration of 24 mg/day B.I.D. of iloperidone for a period of two weeks.

TABLE 2

QT Prolongation and Presence or Absence of a Genotype for SNP_A-2068049,
rs7067971 Associated with a Predisposition to QT Prolongation

| Change Threshold | Low QT | | High QT | | Odds | | | | negative predictive | positive predictive |
|---|---|---|---|---|---|---|---|---|---|---|
| (msec) | −test | +test | −test | +test | Ratio | p value | sensitivity | specificity | value | value |
| QT > 5 | 64 | 0 | 101 | 13 | | 0.969 | 0.11 | 1.00 | 0.39 | 1.00 |
| QT > 15 | 104 | 2 | 61 | 11 | 9.38 | 0.0044 | 0.15 | 0.98 | 0.63 | 0.85 |
| QT > 30 | 144 | 7 | 21 | 6 | 5.88 | 0.0033 | 0.22 | 0.95 | 0.87 | 0.46 |

As can be seen in Table 2, an individual's ABCC2 sequence at the SNP_A-2068049, rs7067971 locus is highly predictive of whether the individual will experience QT prolongation following the administration of iloperidone. For example, using the lowest threshold of a change in QTc interval (between baseline and the end of the second week) greater than 5 milliseconds (normal QTc intervals are between 0.30 and 0.44 seconds for males and between 0.30 and 0.45 for females), 13 of those individuals with the GG genotype (test is considered positive if the genotype for SNP_A-2068049, rs7067971 is GG) experienced QT prolongation while no such individuals did not. The resulting sensitivity (probability that the individual will have a SNP genotype associated with a predisposition to QT prolongation, given that he/she experienced QT prolongation) of 0.11, specificity (probability that the individual will not have a SNP genotype associated with a predisposition to QT prolongation, given that he/she did not experience QT prolongation) of 1.0, negative predictive value (probability that the individual will not experience QT prolongation, given that he/she does not have a SNP genotype associated with a predisposition to QT prolongation) of 0.39, and a positive predictive value (probability that the individual will experience QT prolongation, given that he/she has a SNP genotype associated with a predisposition to QT prolongation) of 1.0, permit one to predict with great accuracy that an individual possessing the GG genotype is likely to experience QT prolongation.

The use of higher thresholds (i.e., QTs greater than 15 and 30 milliseconds) yielded markedly increased negative predictive values (0.63 and 0.87, respectively). The associated decrease in positive predictive values, from 1.0 for QTs greater than 5 milliseconds to 0.46 for QTs greater than 30 milliseconds) suggests that additional factors affect more severe QT prolongation.

As the data in Table 2 show, an individual's ABCC2 sequence at the SNP loci above may be used to predict whether an individual is predisposed to QT prolongation due to the administration of a compound capable of prolonging the QT interval. That is, individuals having a genotype of GG at the rs7067971 locus may reliably be predicted to experience a prolonged QT interval (i.e., a change in QT interval of at least 5 milliseconds) following the administration of a compound capable of prolonging the QT interval. Similarly, individuals having a genotype other than GG at the rs7067971 locus may reliably be predicted to not experience severe QT prolongation (i.e., a change in QT interval of greater than 15 milliseconds) following the administration of a compound capable of prolonging the QT interval.

The ability to make such predictions may be used in deciding whether to treat an individual with a particular compound and/or in determining the dosage appropriate for the individual. For example, an individual predicted to experience QT prolongation may be treated with an alternative compound not known or suspected to cause QT prolongation or may be administered a lower dose of a compound capable of causing QT prolongation than would be administered to an individual not predicted to experience QT prolongation.

The present invention also includes the administration of another compound useful in treating LQTS, in addition to one or more of the compounds above. Compounds useful in treating LQTS and/or preventing cardiac events resulting from LQTS, include, for example, beta blockers, such as propranolol, nadolol, atenolol, metoprolol.

The present invention also includes the prediction of an individual's predisposition for QT prolongation based on one or more of the SNP loci above in combination with the individual's genotype or gene sequence at one or more additional genes or loci. For example, International Patent Application Publication No. WO2006039663, incorporated herein by reference, describes a method of treating an individual with a compound capable of inducing QT prolongation based on the individual's CYP2D6 genotype. Other genotypes and/or gene sequences may similarly be used in combination with the SNP loci above, including those associated with LQTS. It should also be understood that the present invention includes the characterization of an expression product of the ABCC2 gene rather than, or in addition to, the determination of one or more SNP genotypes within the ABCC2 gene. For example, by determining a sequence of an mRNA strand transcribed from the ABCC2 gene, it is possible to determine the sequence of the ABCC2 gene itself and, as described above, determine whether the ABCC2 gene sequence is associated with a predisposition to QT prolongation.

Similarly, by properly characterizing a functional peptide or protein, including the ABCC2 enzyme, translated from the mRNA strand above, it is possible to determine the sequence of the ABCC2 gene itself and, as described above, determine whether the ABCC2 gene sequence is associated with a predisposition to QT prolongation. In addition, the present invention includes determining whether a compound is capable of prolonging a QT interval in an individual. This may be done, for example, by measuring a change in QT interval in a test organism (e.g., human, animal model, cell line) known to possess a ABCC2 genotype associated with a predisposition to QT prolongation following the administration of a quantity of compound under study.

Preferably, the compound is also administered to a test organism known to possess an ABCC2 genotype not associated with a predisposition to QT prolongation.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of administering iloperidone or a metabolite thereof to a human individual, the method comprising:
   determining or having determined the individual's ABCC2 gene sequence at the rs7067971 locus; and
   in the case that the individual's ABCC2 gene sequence at the rs7067971 locus is GG, administering to the individual a first quantity of iloperidone or a metabolite thereof, and
   in the case that the individual's ABCC2 gene sequence at the rs7067971 locus is non-GG, administering to the individual a second quantity of iloperidone or a metabolite thereof, wherein the first quantity is less than the second quantity.

2. The method of claim 1, further comprising: determining the individual's CYP2D6 genotype.

3. The method of claim 1, wherein the method comprises administering iloperidone to the individual.

4. The method of claim 1, wherein the method comprises administering a metabolite of iloperidone to the individual, wherein the metabolite is 1-[4-[3-[4-(6-Fluoro-1,2-benzisoxazol-3-yl)-1-piperidinyl]propoxy]-3-methoxyphenyl]ethanol.

5. A method of administering a compound that is iloperidone or a metabolite thereof to a human individual suffering from long QT syndrome (LQTS), the method comprising:
   determining or having determined the individual's ABCC2 gene sequence at the rs7067971 locus; and
   administering to the individual either a first quantity or a second quantity of the compound based on the individual's ABCC2 gene sequence at the rs7067971 locus,
   wherein the second quantity is larger than the first quantity, and
   wherein the first quantity is administered to the individual if the individual has a GG genotype at the rs7067971 locus, and wherein the second quantity is administered to the individual if the individual has a genotype at the rs7067971 locus that is not GG.

6. The method of claim 5, further comprising:
   determining the individual's CYP2D6 genotype.

7. The method of claim 5, wherein the compound is iloperidone.

8. The method of claim 5, wherein the compound is a metabolite of iloperidone, and wherein the metabolite is 1-[4-[3-[4-(6-Fluoro-1,2-benzisoxazol-3-yl)-1-piperidinyl]-propoxy]-3-methoxyphenyl]ethanol.

9. The method of claim 3, wherein the second quantity of iloperidone is 24 mg/day.

10. The method of claim 7, wherein the second quantity of iloperidone is 24 mg/day.

* * * * *